United States Patent [19]

Morey et al.

[11] Patent Number: 5,293,049
[45] Date of Patent: Mar. 8, 1994

[54] AEROSOL DISCRIMINATOR FOR PARTICLE DISCRIMINATION

[75] Inventors: Richard K. Morey, Tucson; Donald R. Chansky, Jr., Oracle; Douglas J. Wylie, Tucson; Mark A. Mormino, Tucson; Joseph F. Halik, IV, Tucson, all of Ariz.

[73] Assignee: Alliedsignal Inc., Morris Township, Morris County, N.J.

[21] Appl. No.: 927,441

[22] Filed: Aug. 10, 1992

Related U.S. Application Data

[63] Continuation-in-part of Ser. No. 694,188, May 1, 1991, Pat. No. 5,164,604.

[51] Int. Cl.⁵ ............................................. G01N 15/06
[52] U.S. Cl. ................................. 250/574; 356/343; 356/335
[58] Field of Search ............... 250/573, 574, 575; 356/430, 431–439, 339, 335, 343; 340/630

[56] References Cited

U.S. PATENT DOCUMENTS

| | | | |
|---|---|---|---|
| 3,624,835 | 11/1971 | Wyatt | 356/343 |
| 4,420,256 | 12/1983 | Fladda et al. | 356/336 |
| 4,556,873 | 12/1985 | Yamada et al. | 340/630 |
| 4,647,785 | 3/1987 | Morita | 250/574 |
| 4,839,527 | 6/1989 | Leitch | 350/573 |
| 5,164,604 | 11/1992 | Blair et al. | 250/574 |
| 5,194,921 | 3/1993 | Tambo et al. | 356/432 |

OTHER PUBLICATIONS

Article From Dec. 1972 Technical News Bulletin Entitled "New Apparatus Determins Particle Size Distribution in Real Time".
Article From Nov./Dec. 1980 Optical Engineering Entitled "Laser-Based Single Particle Counters for In Situ Particulate Diagnostics" by E. Dan Hirleman.

Primary Examiner—David C. Nelms
Assistant Examiner—A. Davenport
Attorney, Agent, or Firm—Joseph R. Black; Robert A. Walsh

[57] ABSTRACT

An optical particle counter generates a signal indicating an amount of radiation scattered by aerosols in a sample flow. Smoke can be discriminated from other aerosols in the sample flow by analyzing the AC component of the signal. Smoke has a much higher signal-to-noise ratio than that of larger particles such as dust and fog.

24 Claims, 3 Drawing Sheets

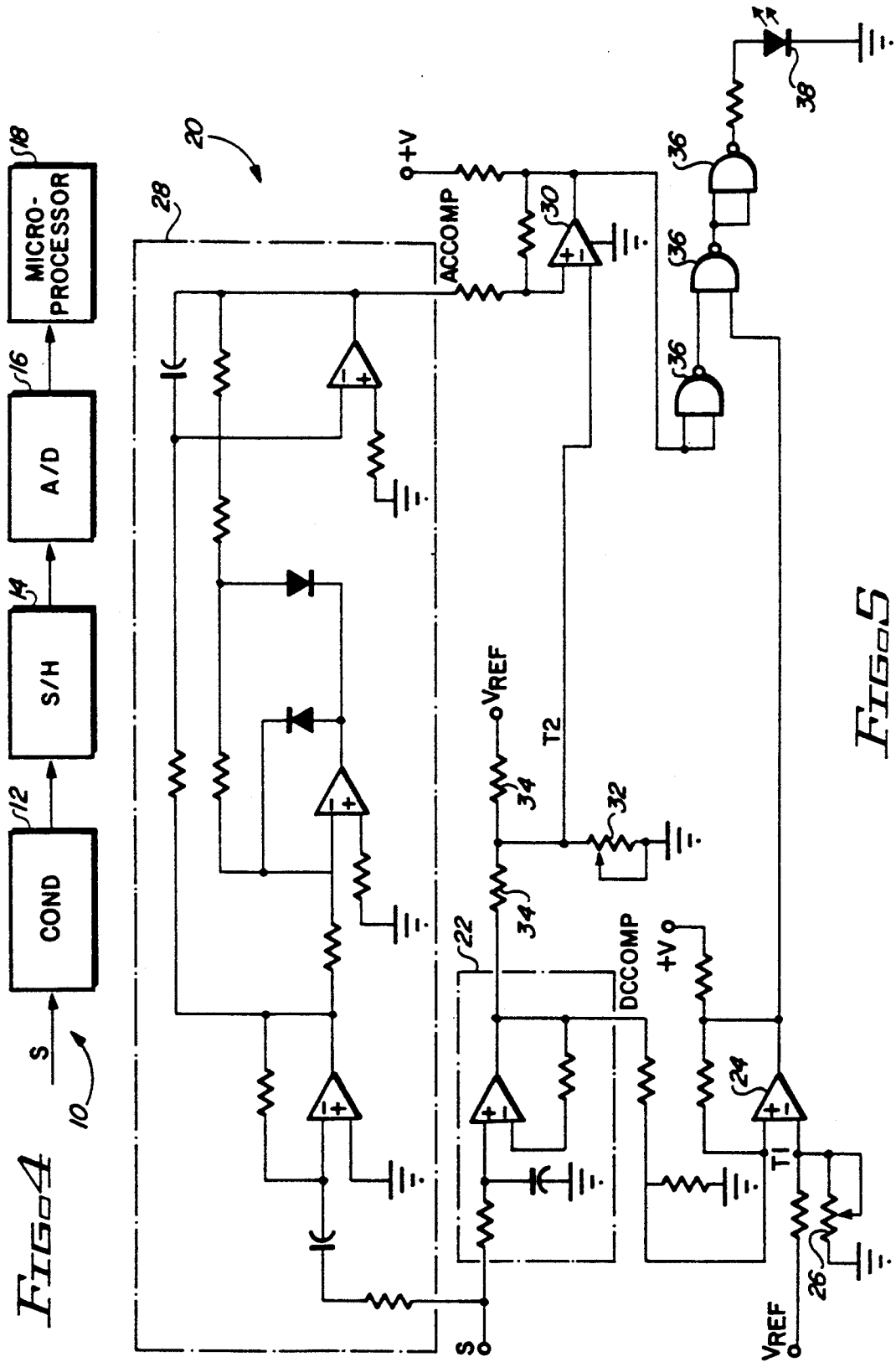

AEROSOL DISCRIMINATOR FOR PARTICLE DISCRIMINATION

This is a continuation-in-part of Ser. No. 07/694,188 filed on May 1, 1991, now U.S. Pat. No. 5,164,604.

BACKGROUND OF THE INVENTION

This invention relates in general to aerosol detection and in particular to apparatus and method of discriminating one type of aerosol from other types of aerosols in a sample flow.

Optical particle counters are well known for their ability to detect the presence of aerosols in sample flows. The optical particle counter (OPC) 2 of FIG. 1 analyzes a sample flow traversing a relatively small optical volume. A source 4 propagates a beam 6 of radiation into the sample flow. The radiation can be collimated or uncollimated. If the sample contains aerosols, such as dust, fog or smoke, the aerosols scatter the radiation from the beam 6. All aerosols scatter the radiation at an angle $\theta$ of 90° from the beam propagation direction. Thus, a photodetector 8 at a 90° angle generates a signal whose amplitude is proportional to the amount of scattered radiation.

The OPC analyzes the sample flow in near real-time. Micron and submicron particles can be sized without affecting the aerosol process. Laser-based OPCs can detect aerosols as small as 0.1 microns.

The OPC of FIG. 1 can be used in a clean room, where aerosols such as smoke and dust cannot be tolerated. Should these aerosols appear in the sample flow, alone or in combination, the OPC triggers an alarm.

However, the OPC cannot discriminate smoke from other aerosols contained in the sample flow. Therefore, the OPC has little utility as a smoke detector when the sample flow contains non-smoke aerosols such as dust. The dust would cause the OPC to trigger a false alarm.

SUMMARY OF THE INVENTION

By analyzing the AC component of the signal from the OPC, one type of aerosol can be discriminated from other types of aerosols in the sample flow. This method can be implemented in both hardware and software.

BRIEF DESCRIPTION OF THE DRAWINGS

FIG. 4 is a schematic diagram of digital apparatus for implementing the method shown in FIG. 2; and FIG. 5 is a schematic diagram of analog apparatus for implementing the method according to the present invention.

DETAILED DESCRIPTION OF THE PREFERRED EMBODIMENTS

Figure 1:
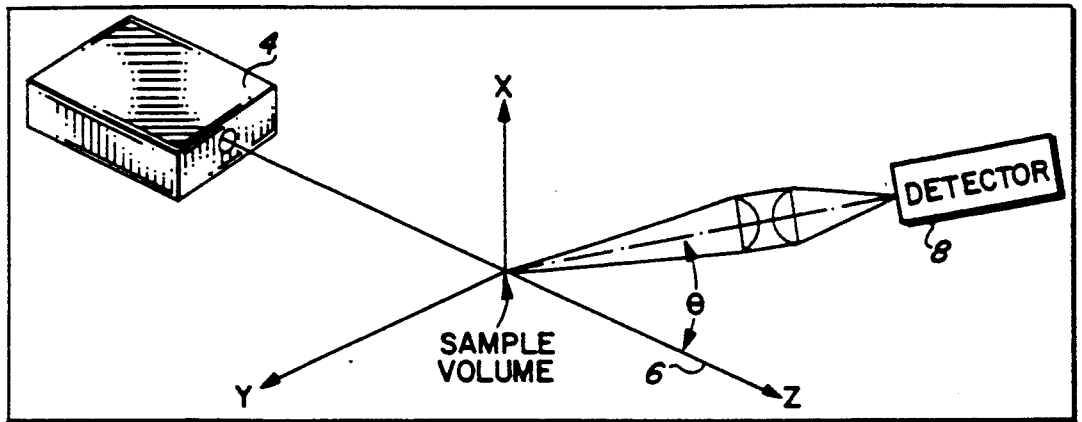
FIG. 1 is a schematic diagram of an OPC known to the prior art.

The following method is utilized in conjunction with an OPC that provides a signal whose amplitude indicates an amount of radiation scattered by aerosols in a sample flow. One type of OPC is shown in FIG. 1. This OPC provides a signal whose amplitude indicates scattering at a single angle. Another type of OPC is disclosed in U.S. Pat. No. 5,164,604 and assigned to Allied-Signal Inc., the assignee of the present invention. This laser-based OPC provides a signal whose amplitude indicates a ratio of scattering at two different angles.

Figure 2:
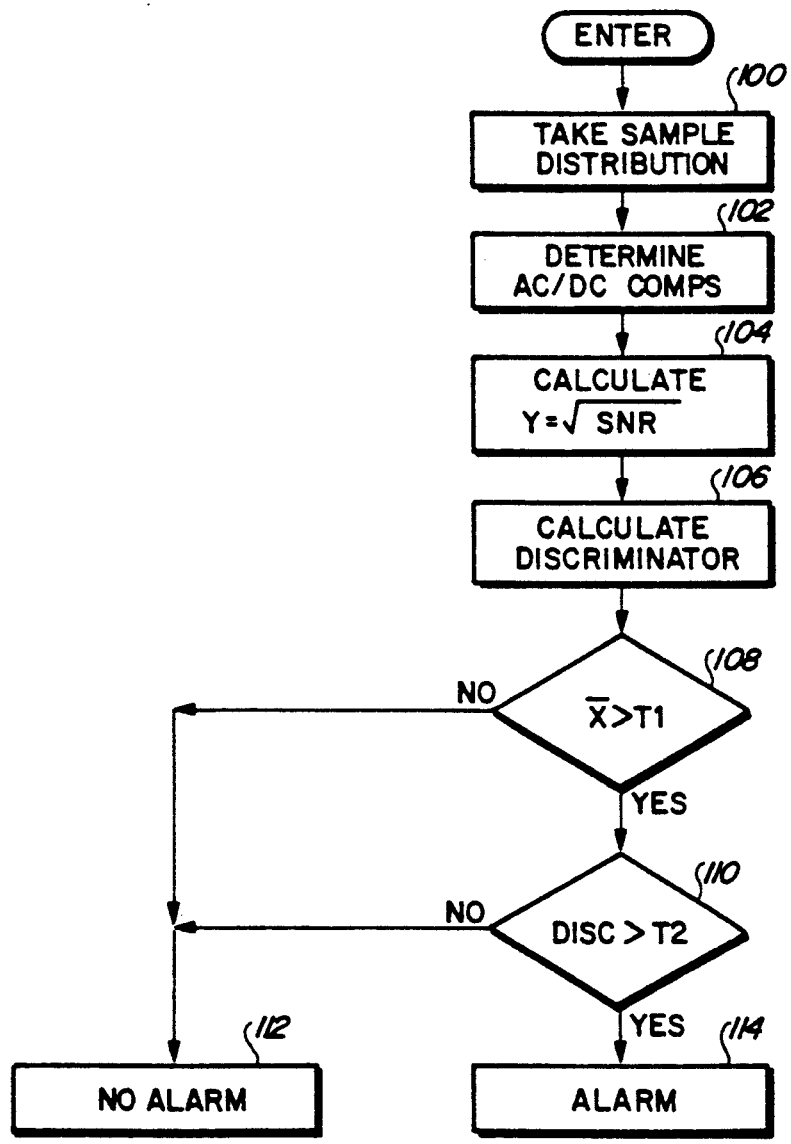
FIG. 2 is a flowchart of an aerosol discrimination method according to the present invention.

FIG. 2 shows the method of analyzing the OPC signal S to determine whether a certain type of aerosol is contained in the sample flow. The OPC signal S is analyzed by examining its AC and DC components. The DC component is proportional to the obscuration caused by the particles in the sample flow, and the AC component is proportional to the size of the particles in the sample flow.

This method is particularly suitable for discriminating smoke from larger aerosols such as dust and fog. Accordingly, the method will be described in connection with smoke detection.

In step 100, a sample distribution is formed from the OPC signal S. For example, the distribution could consist of ten samples of the OPC signal S. The samples of an ideal distribution correspond to radiation scattered by entirely different particles. To prevent multiple samples of the same particle from being taken, the sampling rate is established according to the linear velocity of the sample flow, i.e., the velocity at which the particles pass by the detector of the OPC. For example, a linear velocity of three feet per minute would require a sampling rate of 50 Hz. Higher flow rates allow the samples to be taken in a shorter period of time and, therefore, allow for quicker detection of smoke.

In step 102 the spectral content of the sample distribution is analyzed. For the exemplary sample distribution above, the AC and DC components are determined once every 200 ms. A linear regression routine such as a least squares fit provides a mean XBAR and variance VAR for the distribution. The mean XBAR is proportional to the DC component of the signal S; it indicates the amount of obscuration caused by the aerosols in the sample distribution. The variance VAR is proportional to the AC component; it is believed to indicate the particle size in the sample distribution. It has been found that sample distributions containing smaller aerosols have smaller variances than do larger aerosols.

Alternatively, the AC and DC components of the sample distribution can be determined by a Fast Fourier Transform (FFT). The AC component would be the sum of the fundamental and harmonic frequencies. However, such in-depth analysis of the AC component is not required; therefore, the mean XBAR and variance VAR of the least squares fit is preferred over the statistics provided by the FFT.

In step 104, a square Y of the signal-to-noise ratio SNR is calculated. The ratio SNR can be calculated as $(XBAR)^2/VAR$. It has been found that the square Y of the signal-to-noise ratio SNR provides a better indicator of aerosol size than does the variance VAR.

In step 106, a discriminator DISC is calculated from the square Y of the signal-to-noise ratio SNR. Given the small number of samples in the distribution, the mean XBAR and variance VAR are sensitive to a high rate of change in the OPC signal S. To reduce this sensitivity, the square Y of the signal-to-noise ratio SNR is passed through a low pass filter. This filter can be an infinite impulse response type that calculates the discriminator as follows:

$$DISC = DISC_O + FRAC(Y - DISC_O)$$

where $DISC_O$ is the value of the discriminator for the previous sample distribution and FRAC has a value between 0 and 1. The value FRAC controls the amount of change between successive discriminators. It is inversely proportional to the size of the sample distribution since sensitivity is reduced as the number of samples is increased.

In the event a large distribution is sampled, the low pass filter can eliminated. As the size of the distribution is increased, the ability to discriminate smoke from other aerosols is improved. However, a large distribution may not always be desirable because it requires a longer time to collect samples. Involved is a tradeoff of accuracy versus speed.

Steps 108 and 110 determine whether there is sufficient smoke in the sample flow to warrant an alarm. The mean XBAR is compared to a first threshold T1 which establishes the maximum allowable amount of aerosols in the sample flow (step 108). If this threshold T1 is not exceeded, then there is insufficient aerosol in the sample flow to warrant an alarm, regardless of whether smoke is found in the sample flow. Therefore, an alarm condition is not indicated (step 112).

If, however, the sample flow contains a sufficient amount of aerosols, the discriminator DISC is compared to a second threshold T2 (step 110). If this threshold T2 is not exceeded, the sample flow contains aerosols other than smoke. However, if the second threshold T2 is also exceeded, the sample flow contains smoke in sufficient quantity to warrant an alarm condition (step 114).

This method is illustrated by the following four cases. In the first case, the sample flow is clean, i.e., free of aerosols. Because there are no particles to scatter radiation, the mean XBAR of the samples in the distribution is small. The variance VAR is also small; therefore, the discriminator DISC is very large.

In the second case, the sample flow contains only smoke. The resulting distribution has a relatively small variance VAR, which drives the discriminator DISC to a large value. As the number of smoke particles in the sample flow is increased, the mean XBAR of the distribution becomes larger.

In the third case, the sample flow contains only dust. The resulting distribution has a variance VAR that is approximately two orders of magnitude larger than the variance VAR for the smoke. Thus, the discriminator DISC for smoke is significantly larger than that for dust. As the number of dust particles in the sample flow is increased, the mean XBAR becomes larger.

In the fourth case, the sample flow contains a mixture of dust and smoke. The smaller smoke particles reduce the variance VAR of the distribution; therefore, the discriminator DISC is still at least two orders of magnitude greater than that for a sample containing only dust.

The values for the thresholds T1 and T2 are established according to the physical characteristics of the application. For example, a clean room must be free of smoke and dust; therefore, the first threshold would be extremely small. The second threshold would be irrelevant. In contrast, a communications switching room would allow for a lot of dust and only low levels of smoke. Therefore, the first and second thresholds T1 and T2 would have large values.

Actual values for the thresholds T1 and T2 are determined empirically. For example, dark gray smoke could be injected into a test atmosphere at a level that constitutes an alarm condition (e.g., 3%). The resulting mean XBAR and discriminator DISC would be saved as the first and second thresholds T1 and T2. Thus, any type of aerosol can be detected simply by selecting proper values for the thresholds T1 and T2.

Figure 3:
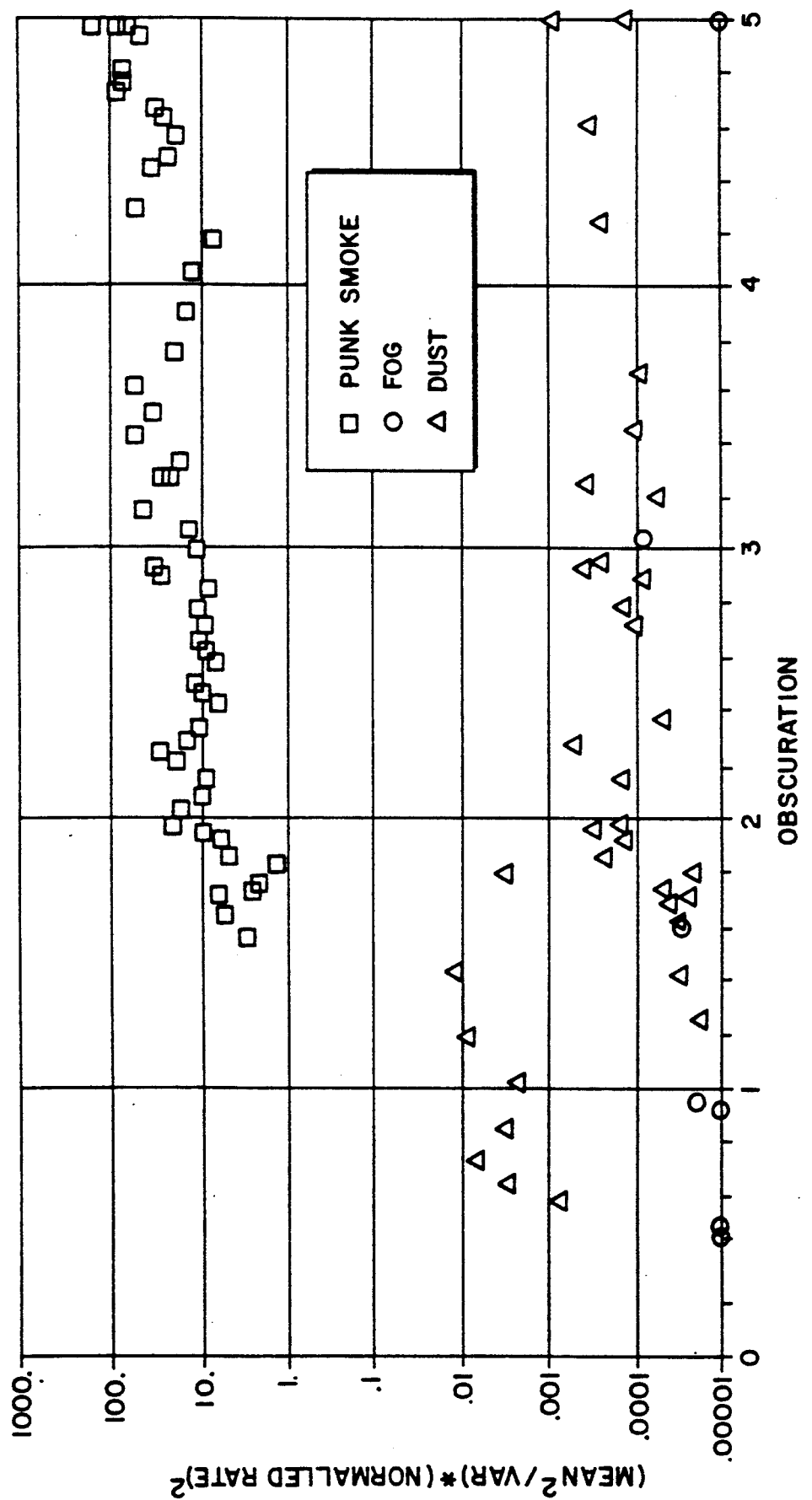
FIG. 3 is a plot of scattering characteristics of various aerosols.

The plot of FIG. 3 compares the scattering characteristics for smoke, fog and dust. A 780 nm laser beam was propagated into a sample flow, and scattering was measured at 90°. Discriminators were calculated and normalized for flow rates. Clearly the normalized discriminator for smoke is several orders of magnitude larger than for the discriminators for dust and fog.

FIG. 4 shows digital apparatus 10 for detecting smoke. The OPC signal S is processed by a signal conditioner 12, sampled by a sample and hold (S/H) 14 and converted to digital words by an A/D converter 16. A microprocessor 18 processes the digital words according to the flowchart of FIG. 2. The microprocessor 18 can be an Intel 80196, which includes a built-in A/D converter.

FIG. 5 shows analog apparatus 20 for detecting smoke. The OPC signal S is filtered by a low pass filter 22, which can be realized by a capacitor, two resistors and an operational amplifier. An output of this filter 22 provides a signal DCCOMP indicating the DC component of the OPC signal S. The signal DCCOMP is compared to the first threshold T1 by a comparator 24. The first threshold T1 is set by a first potentiometer 26.

To determine its AC component, the OPC signal S is also filtered by a band pass filter 28. For flow rates of three feet per minute, the filter's pass band is centered at a frequency of roughly 50 Hz, and its lower and upper cutoff frequencies are roughly 2 and 98 Hz, respectively. Most of the energy of the AC component is contained within this bandwidth. The lower cutoff frequency is set as low as possible, and the upper cutoff frequency is limited by the internal characteristics (e.g., capacitance) of the filter 28. The pass bands for different flow rates would be centered at higher frequencies. The filter 28 then rectifies the filtered signal to produce the signal ACCOMP, which indicates the AC component of the OPC signal S. The band pass filter 28 can be realized by two capacitors, three operational amplifiers, five resistors, and two diodes.

The signal ACCOMP is compared to the second threshold T2 by a second comparator 30. The second threshold T2 is set by a second potentiometer 32, and it is self-adjusted according to the characteristic of the aerosol. For smoke, the signal ACCOMP becomes larger as the total content of the smoke in the sample flow is increased. For example, the signal ACCOMP for a sample flow containing 1% smoke is between 50 and 100 millivolts. When the smoke content is increased to between 3% and 4% smoke, the signal ACCOMP increases to 200 millivolts. The adjustment is performed by pulling up the second threshold T2 with the signal DCCOMP and voltage dividers 34.

An alarm condition is determined by three NAND gates 36 which are responsive to the outputs of the first and second comparators 24 and 30. When both thresholds T1 and T2 are exceeded, an LED 38 is illuminated.

The analog apparatus 20 offers several advantages over the digital apparatus 10. Because the OPC signal S does not have to be converted from analog to digital, the analog apparatus 20 is not affected by resolution error. Processing is also faster. Further, the analog apparatus 20 is not affected by offset accumulation, which is caused by a build-up of contaminants in the OPC. These contaminants scatter light, thereby increasing the DC component of the OPC signal S.

It will be understood that the embodiments described herein are merely exemplary and that a person skilled in the art may make many modifications and variations without departing from the spirit and of the present invention. All such modifications are intended to be included within the scope of the present invention as defined by the appended claims.

We claim:

1. A method of analyzing a scatter signal from an optical particle counter, said scatter signal indicating an amount of radiation scattered by a sample flow, said method comprising the steps of:

determining the AC component of said scatter signal; and comparing said AC component to a reference signal indicating the amount of scatter caused by a particular aerosol.

2. The method of claim 1, wherein said AC component is determined by taking samples of said scatter signal; and by performing a statistical analysis on said samples.

3. The method of claim 2, wherein said statistical analysis is performed by forming a distribution of said samples; and generating a signal indicating a variance of said distribution.

4. The method of claim 3, wherein said variance signal is determined from a least squares fit.

5. The method of claim 3, further comprising the step of calculating a discriminator signal from said variance signal.

6. The method of claim 5, further comprising the step of filtering said discriminator signal.

7. The method of claim 1, wherein said AC component is determined by taking a sample distribution of said scatter signal; taking a FFT of said distribution to determine fundamental and harmonic frequencies; and summing said fundamental and harmonic frequencies.

8. The method of claim 1, further comprising the step of determining the DC component of said scatter signal to indicate obscuration caused by all aerosols in said sample flow.

9. The method of claim 1, wherein said AC component is determined by filtering said scatter signal.

10. The method of claim 9, wherein said scatter signal is band pass filtered.

11. The method of claim 10, further comprising the steps of rectifying said filtered signal; and comparing said rectified signal to a second reference signal.

12. The method of claim 11, further comprising the step of adjusting said second reference signal according to the characteristic of said particular aerosol.

13. The method of claim 9, further comprising the step of filtering said scatter signal to determine its DC component, said DC component indicating obscuration caused by all aerosols in said sample flow.

14. Apparatus for analyzing a scatter signal from an optical particle counter, said scatter signal indicating an amount of radiation scattered by a sample flow, said apparatus comprising:

sampling means for sampling said scatter signal;

first processing means, responsive to said sampling means, for forming a distribution of samples;

second processing means, responsive to said first processing means, for generating a signal indicating a variance of said distribution;

third processing means, responsive to said second processing means, for generating a discriminator signal from said variance signal; and comparing means, responsive to said third processing means, for comparing said discriminator signal to a reference signal.

15. The apparatus of claim 14, wherein said third processing means also filters said signal discriminator.

16. The apparatus of claim 14, further comprising fourth processing means, responsive to said first processing means, for generating a signal indicating a mean of said distribution, wherein said comparing means also compares said mean signal to another reference signal.

17. The apparatus of claim 16, wherein a microprocessor includes said comparing means and said first, second, third and fourth processing means.

18. Apparatus according to claim 14, wherein said reference signal indicates presence of smoke in said sample flow, whereby said apparatus is a smoke detector.

19. Apparatus for analyzing a scatter signal from an optical particle counter, said scatter signal indicating an amount of radiation scattered by a sample flow, said apparatus comprising:

band pass filter means for determining the AC component of said scatter signal; and first comparing means, responsive to an output of said band pass filter means, for comparing said AC component to a first reference signal corresponding to a particular aerosol.

20. The apparatus of claim 19, further comprising:

low pass filter means for determining the DC component of said scatter signal; and second comparing means, responsive to an output of said low pass filter means, for comparing said DC component to a second reference signal;

21. The apparatus of claim 20, further comprising adjusting means, responsive to said low pass filter means, for adjusting said first reference signal with said DC component.

22. The apparatus of claim 20, wherein said particular aerosol is smoke, and wherein said band pass filter means has a lower cutoff frequency of roughly 2 Hz.

23. The apparatus of claim 22, wherein said band pass filter means is centered about a frequency of approximately 50 Hz.

24. The method of claim 5, wherein said discriminator signal is calculated by:

determining the DC component of said scatter signal; and taking the ratio of the square of said DC component over said variance.

* * * * *